(12) United States Patent
Criton et al.

(10) Patent No.: US 6,464,637 B1
(45) Date of Patent: Oct. 15, 2002

(54) AUTOMATIC FLOW ANGLE CORRECTION BY ULTRASONIC VECTOR

(75) Inventors: Aline Laure Criton, Seattle, WA (US); Helen Frances Routh, Seattle, WA (US)

(73) Assignee: Koninklijke Philips Electronics N.V., Eindhoven (NL)

(*) Notice: Subject to any disclaimer, the term of this patent is extended or adjusted under 35 U.S.C. 154(b) by 63 days.

(21) Appl. No.: 09/721,301

(22) Filed: Nov. 21, 2000

Related U.S. Application Data

(60) Provisional application No. 60/213,786, filed on Jun. 23, 2000.

(51) Int. Cl.[7] .............................................. A61B 8/00
(52) U.S. Cl. ...................................... 600/441; 600/454
(58) Field of Search ......................... 600/441, 453–457; 73/625, 626

(56) References Cited

U.S. PATENT DOCUMENTS

| 4,265,126 | A | * | 5/1981 | Papadofrangakis et al. . 600/441 |
| 4,416,286 | A | | 11/1983 | Iinuma et al. |
| 5,551,434 | A | * | 9/1996 | Iinuma ........................ 600/455 |
| 5,555,886 | A | * | 9/1996 | Weng et al. ................. 600/454 |
| 5,606,972 | A | * | 3/1997 | Routh ......................... 600/455 |
| 5,855,557 | A | * | 1/1999 | Lazenby ...................... 600/443 |
| 5,910,119 | A | | 6/1999 | Lin |
| 5,928,153 | A | | 7/1999 | Chiang et al. |
| 5,944,666 | A | * | 8/1999 | Hossack et al. ............. 600/454 |
| 6,142,944 | A | | 11/2000 | Li et al. |
| 6,193,665 | B1 | * | 2/2001 | Hall et al. ................... 600/455 |
| 6,196,972 | B1 | * | 3/2001 | Moehring .................... 600/441 |

* cited by examiner

*Primary Examiner*—Marvin M. Lateef
*Assistant Examiner*—Ali M. Imam
(74) *Attorney, Agent, or Firm*—W. Brinton Yorks, Jr.

(57) ABSTRACT

An ultrasound system produces an image including a blood vessel. A blood flow direction indicator is displayed over the blood vessel to indicate the direction of blood flow within the vessel. The direction of blood flow is used to correct the Doppler estimate for angle of insonation. The orientation of the blood flow direction indicator is set automatically by a vector processor. The automatically calculated angle is used to display the correct flow velocity without user intervention.

28 Claims, 3 Drawing Sheets

US 6,464,637 B1

AUTOMATIC FLOW ANGLE CORRECTION BY ULTRASONIC VECTOR

This application claims the benefit of Provisional U.S. patent application Ser. No. 60/213,786, filed Jun. 23, 2000.

This invention relates to ultrasonic diagnostic systems which measure blood flow by the Doppler technique and, in particular, to such systems in which the error due to the angle between the blood flow direction and the Doppler beam is automatically corrected by a vector processing technique.

Doppler ultrasound has long been used to quantify and image blood flow in the body. However, such measurements are angle-sensitive because ultrasonic blood flow velocity estimation is limited to the velocity component along the ultrasound beam axis. Although conventional Doppler analysis has great clinical utility, logical applications for Doppler velocity measurements have proven unreliable when existing instruments are used in an attempt to quantify the velocity of blood flow through an artery or vein. The ultrasonic Doppler technique will accurately measure flow which is in line with (parallel to) the axis of the Doppler beam. However, it is usually not possible to orient the Doppler beam for this alignment, particularly for superficial vessels which are substantially parallel to the skinline. This gives rise to an error in the measured velocity which is a function of the angle between the Doppler beam and the direction of flow. The conventional way to account for this error is for the clinician to set a cursor in alignment with the axis of the vessel, then use the angle between this cursor and the Doppler beam to correct the measurement. The papers "Physiological Pulsatile Flow Experiments in a Model of the Human Aortic Arch" by T. L. Yearwood and K. B. Chandran, publ. in *Journal of Biomechanics*, vol. 15, No. 9, pp 683–704, (1984) and "Hemodynamics of the Normal Human Carotid Bifurcation: In Vitro and In Vivo Studies" by D. N. Ku, D. J. Phillips, D. P. Giddens, and D. E. Strandness, publ. in *Ultrasound in Medicine and Biology*, vol. 11, pp 13–26, (1985), as well as the more recent paper "Spiral laminar flow in Arteries" by P. A. Stonebridge and C. M. Brophy, publ. in *The Lancet*, vol. 338, Nov. 30, 1991 at pp 1360–1361, have shown that the normal flow in most arteries is helical, not parallel to the vessel axis, due to the effect of the bends and bifurcations in the artery. Although blood does flow parallel to the walls of an artery in the regions near it walls, this does not mean that velocities are parallel to the axis of the artery throughout the vessel. Thus, it is not possible, using the cosine of the angle between the Doppler ultrasound beam and the vessel axis, to determine correctly the magnitude of the velocity from the vector component projected onto the ultrasound beam. Moreover the hemodynamics of the flow get even more complex in pathological arteries, due to atherosclerotic obstructive disease. Other diseases such as deep venous thrombosis of the leg (abnormal proximal venous obstruction) or venous valvular incompetence of the leg (abnormal venous reflux) or aortic valve stenosis, or cardiac valve regurgitation can generate complex flow patterns as well, for which the vessel-aligned cursor does not yield an accurate velocity measurement.

In accordance with the principles of the present invention, a technique is presented by which the angle of the blood flow or tissue motion is automatically calculated and displayed in real time to the user in pulsed wave Doppler. It is thereby possible, using the cosine of this calculated angle to determine correctly the magnitude of the velocity of the blood flow or tissue motion. The inventive technique utilizes an ultrasonic transducer array in a crossbeam configuration capable of resolving two orthogonal components of the velocity vector. Velocity vectors determined by the two beams are used to resolve a true velocity vector, and this vector is used to automatically set the orientation of the motion cursor on the ultrasonic image of the vessel. The clinician may accept the automatic cursor placement as the direction of flow or motion, may manually alter its orientation, or may compare velocities calculated from the automatically placed motion cursor with those calculated from a cursor manually oriented by the clinician. Other techniques for determining the direction of fluid or tissue motion are also described.

Figure 1:
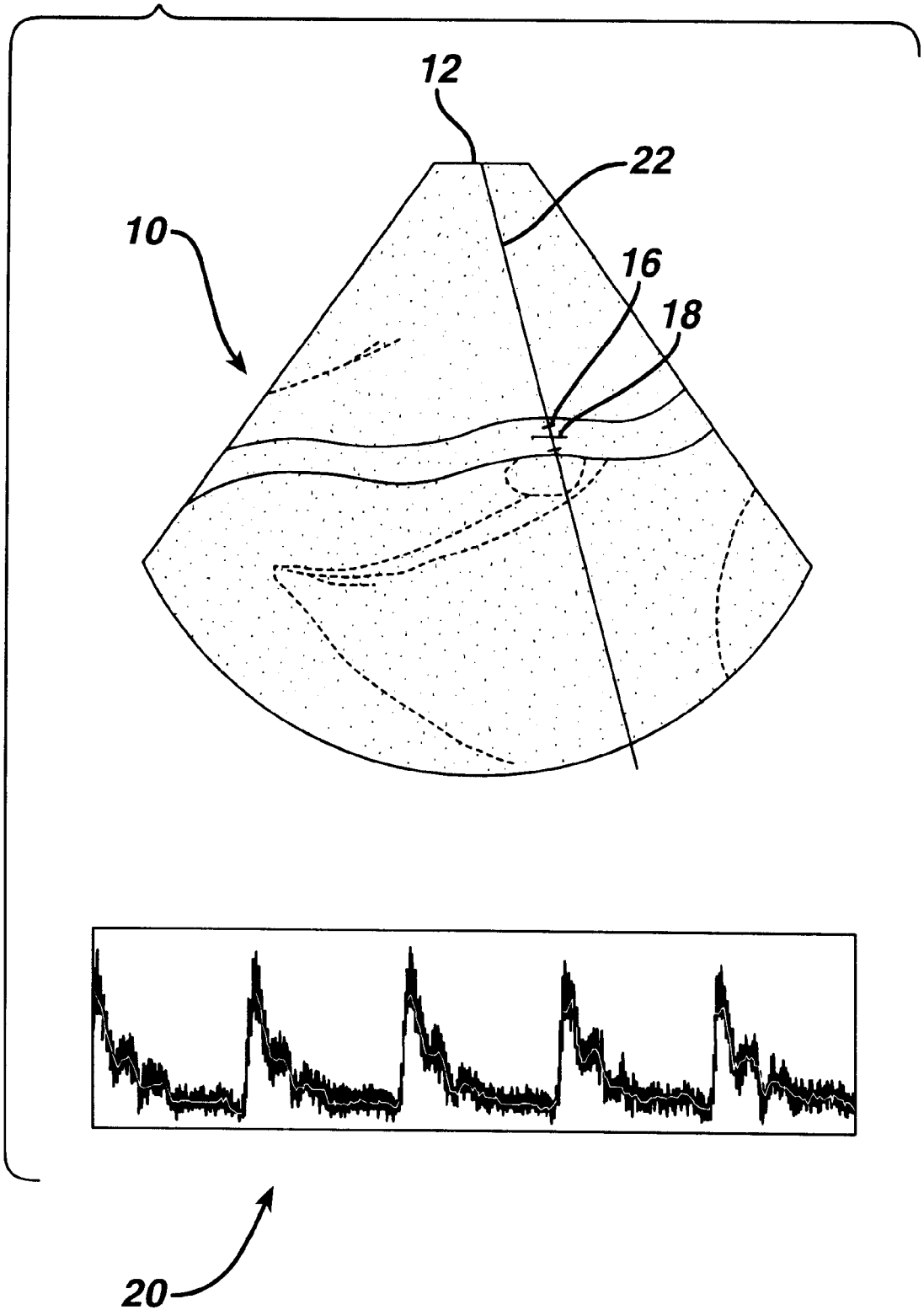
FIG. 1 shows a duplex spectral Doppler display.

A duplex spectral Doppler display is shown in FIG. 1. An ultrasonic image 10 is produced by an electronically steered array transducer (e.g., steered linear transducer) located at the top of the image 12. The image shows a blood vessel 14 in which blood flow velocities are to be measured. A line 22 in the image marks the direction of a transmit Doppler beam which is steered to intersect the desired measurement location in the vessel 14. A sample volume cursor 16 is placed on the vessel with the point of the measurement bounded by the cursor 16. The cursor 16 includes a flow direction cursor 18. In the conventional practice the clinician will manually adjust a control on the ultrasound system until the flow direction cursor 18 is aligned parallel to the walls of the vessel 14, relying on the assumption that the blood is flowing in the sample location parallel to the vessel walls, as the drawing illustrates. Doppler measurements are taken by pulsed Doppler along the beam direction 22 at the sample volume location and the estimated velocities are adjusted for the angle between the beam line 22 and the flow direction cursor 18. The estimated velocities are displayed in a spectral Doppler format as shown at 20.

Figure 2:
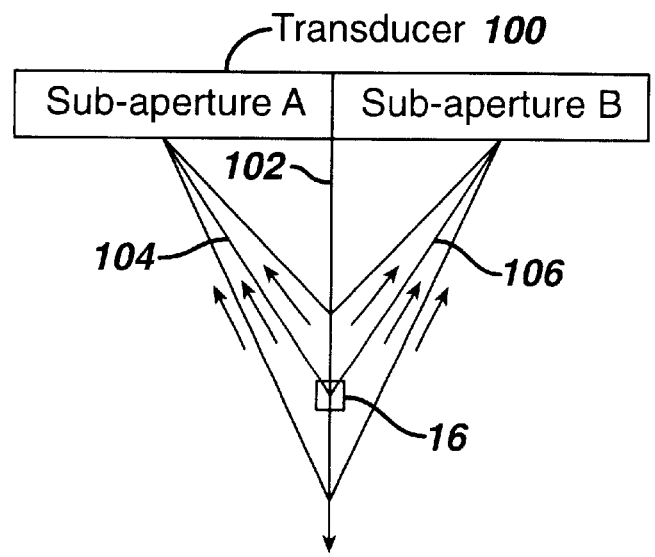
FIG. 2 illustrates crossbeam reception for a transmit beam steered normal to a transducer array.
Figure 3:
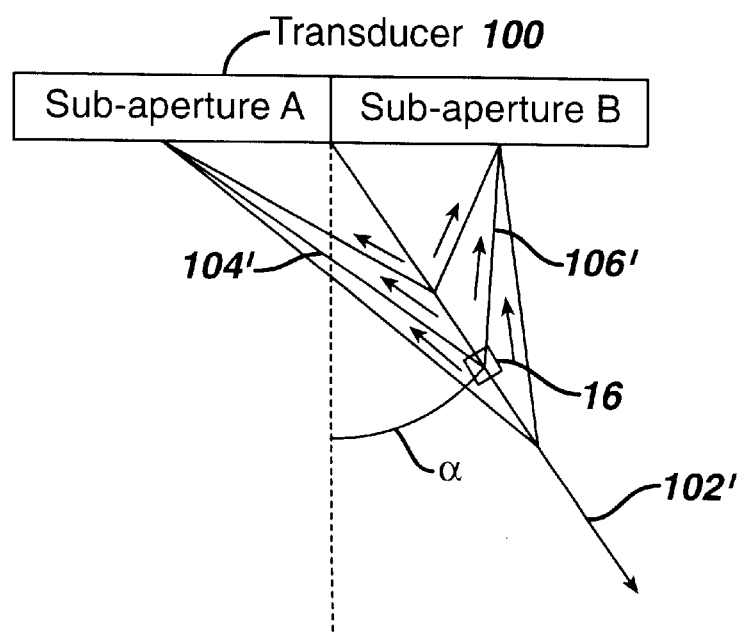
FIG. 3 illustrates crossbeam reception for a transmit beam steered at a non-orthogonal angle to a transducer array.

The principle of the present invention is illustrated by FIGS. 2 and 3. A Doppler beam is transmitted along the beam line 102 using some or all of the elements of a transducer array 100. The full aperture (of all of the array elements in this example) may be used to transmit the steered and focused Doppler beam along the beam line. The elements of the array 100 are divided into left and right receiver sub-arrays denoted as Sub-aperture A and Sub-aperture B. The locations of the sub-apertures on either side of the array center are preferably variable such that straight lines between any observation point in the field of view can have equal angles with respect to a straight line between the region of interest and the center of the transmitter sub-array, although equal angles are not necessary so long as the two angles differ and are known. The sub-apertures receive echo signals from a point or points chosen along the beam line 102, in this case receiving echoes from the sample volume 16 along receive beam paths 104 and 106. By reason of the separation of the sub-aperture centers each receive beam path has its own angle with respect to the beam line 102 and hence with respect to the direction of blood flow at the sample volume location. In FIG. 2 the transmitted beam is normal to the face of the transducer. FIG. 3 illustrates the case when the Doppler beam 102' is steered at an angle a with respect to the normal axis. Again, each sub-aperture has a receive path 104', 106' with its own unique angle to the transmit beam direction 102' and the direction of flow at the sample volume 16.

An embodiment of the present invention resolves the axial velocity component in the acoustic beamsteering direction and the transverse component at right angles to the beamsteering direction. The ensemble of echo signals received by each sub-array are processed by Fourier transformation to estimate the mean frequency of the Doppler spectrum using a form of the expression $$\Delta f = \frac{2v f_0 \cos\theta}{c}$$

where $v \cos \theta$ is the component of velocity along the transmit beam axis. If $\vec{K}_0$ is a unit vector in the direction of the transmitted ultrasound wave vector, and $\vec{K}_1$ and $\vec{K}_2$ are the unit center ultrasound wave vector for the two receiving directions, the Doppler frequency shifts $\Delta f_1$ for the Sub-aperture A and $\Delta f_2$ for the Sub-aperture B can be written as:

$$\Delta f_1 = \frac{f_0}{c} * (\vec{K}_1 - \vec{K}_0) \cdot \vec{v} \quad \text{and} \quad \Delta f_2 = \frac{f_0}{c} * (\vec{K}_2 - \vec{K}_0) \cdot \vec{v}$$

where $f_0$ is the transmit frequency, c is the ultrasound propagation speed (1540 m/s) and $\vec{v}$ is the vector velocity of the blood flow. If $\vec{K}_1$ and $\vec{K}_2$ are symmetrical with respect to $\vec{K}_0$ the difference $(\vec{K}_2 - \vec{K}_1)$ is parallel to the transverse component of the velocity, i.e., the component at right angles to the transmit beam direction. Also the sum ($\vec{K}_1 + \vec{K}_2$) is proportional to $\vec{K}_0$. The transverse component of velocity is given by $$v_t = \frac{(\vec{K}_2 - \vec{K}_1) \cdot \vec{v}}{2\sin(\phi)} = \frac{c}{f_0 * 2 * \sin(\phi)} (\Delta f_2 - \Delta f_1)$$

and the beam direction component by $$v_b = \frac{(\vec{K}_2 + \vec{K}_1) \cdot \vec{v} + 2\vec{K}_0 \cdot \vec{v}}{2\sin(\phi)} = \frac{c}{f_0 * 2 * \sin(\phi)} (\Delta f_1 + \Delta f_2)$$

where $\phi$ is angle between the transmit wave vector $\vec{K}_0$ and $\vec{K}_1$.

The Doppler angle $\theta$ can be derived from the transverse and beam component of the velocity by $$\theta = \arctan\left(\frac{v_t}{v_b}\right) = \arctan\left(\frac{\Delta f_2 - \Delta f_1}{\Delta f_1 + \Delta f_2}\right)$$

Figure 4:
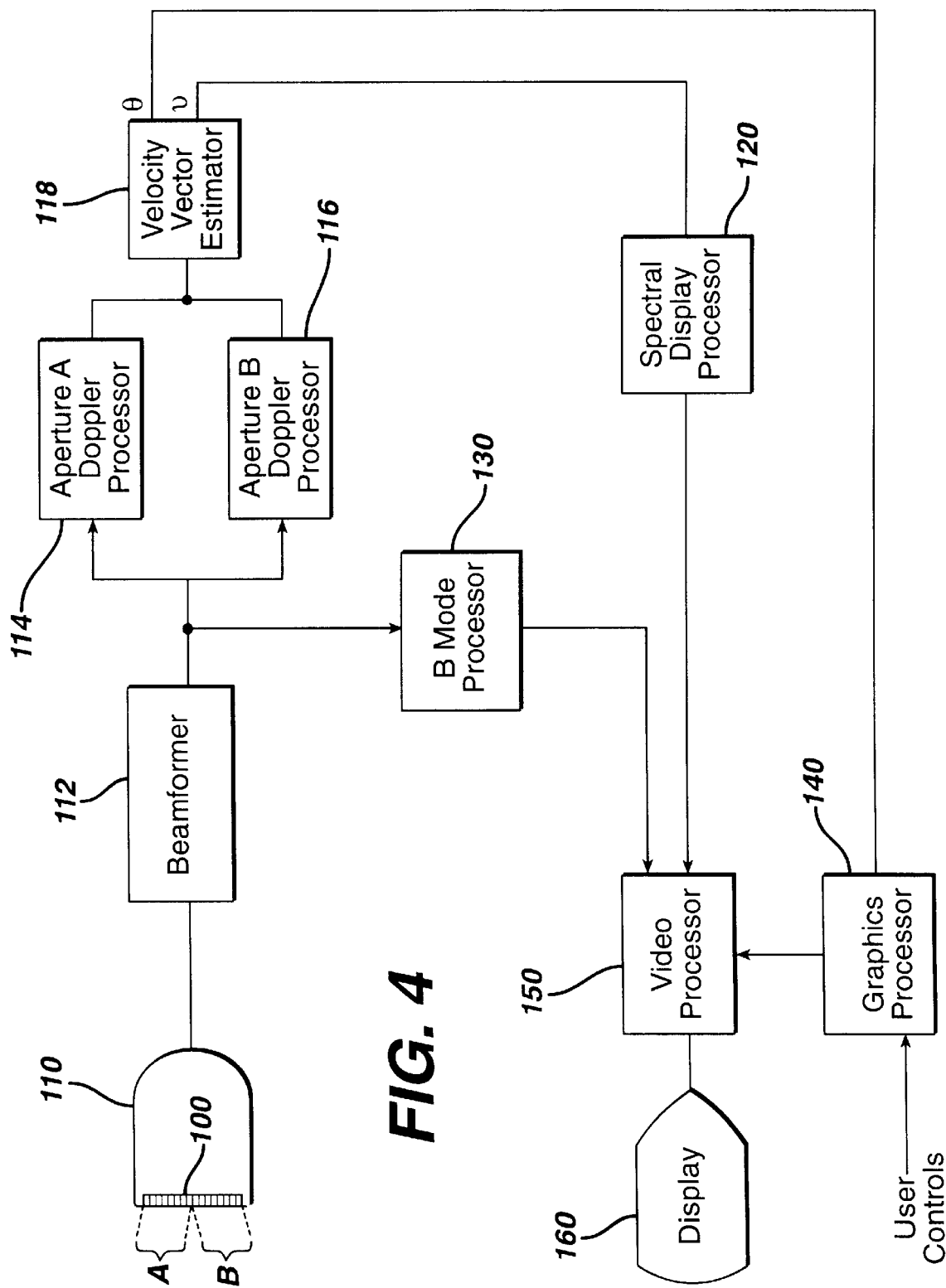
FIG. 4 illustrates in block diagram form an ultrasound system constructed in accordance with the principles of the present invention.

FIG. 4 illustrates an ultrasound system constructed in accordance with the present invention. A beamformer 112 has a plurality of channels coupled to the elements of the array transducer 100. In the transmit mode the beamformer controls the time of actuation of the elements of the array transducer 100 to transmit a Doppler beam in the desired beam direction (as indicated by the beam line 22 on the ultrasound display) and focused at the sample volume location selected by placement of the sample volume cursor 16 by the clinician. In a constructed embodiment all of the array elements are used for transmission. During reception the echo signals from the sample volume are received by division of the elements of the array into sub-apertures A and B. The echoes received by the sub-aperture A elements are processed by the beamformer receive channels coupled to those elements, and the echoes received by the sub-aperture B elements are processed by the beam former receive channels coupled to the sub-aperture B elements. The signals of the two sub-apertures are Doppler processed as explained above by the aperture A Doppler processor 114 and the aperture B Doppler processor 116, the outputs of which are then combined by a velocity vector estimator which calculates the true Doppler velocity vector as described above. The velocity information produced by the velocity vector estimator is used by the spectral display processor 120 to produce signals for a spectral Doppler display 20 (FIG. 1), and the Doppler angle $\theta$ is coupled to a graphics processor 140 where it is used to automatically set the orientation used to display the flow direction cursor 18 with respect to the beam direction line 22. The Doppler beams are time-interleaved with the transmission and reception of B mode scanlines used by a B mode processor 130 to produce the ultrasound image 10 on which the sample volume and flow direction cursors are displayed. The ultrasound image may also be a colorflow Doppler image if desired.

While an embodiment of the present invention will estimate true flow velocities and Doppler angles $\theta$, the orientation of the flow direction cursor may appear to be incorrect to a user who is accustomed to seeing the cursor parallel to the vessel walls. The graphics processor 140 therefore is responsive to a user control by which the user may manually reset the flow direction cursor from the position determined by the system. Alternatively, the user may place her own flow direction cursor manually over the automatically displayed cursor. Two spectral displays may be shown, one using the velocities determined by the system and another corrected by the angle set by the user's cursor, enabling the clinician to compare the resultant velocities of the two. The comparison may also be shown as a spectral display with two mean velocity traces, one from the automatically determined vector and another corrected in correspondence with the user's manually set cursor.

Numerous variations and additions to the inventive technique are possible. Instead of using Doppler signals from two sub-apertures for the Doppler vector estimation, three or more sub-apertures may be employed. Three sub-apertures can be used to estimate the velocity and flow direction in a three dimensional image, for instance. At least two of the three sub-apertures must not be co-aligned to detect the direction of motion in a three dimensional image field. A motion estimation technique may be used for the vector estimation such as one which performs speckle tracking of the blood cells. When speckle tracking is used to find the direction of motion, the speckle pattern of the moving blood cells or tissue resulting from the coherency of the ultrasound beam is tracked over time as the cells or tissue move. Beam modulation techniques such as spatial quadrature detection may also be used to determine the motion vector. In the spatial quadrature technique the beam is modulated in the transverse direction to obtain a phase shift arising from the transverse motion of tissue or flow. The axial component of motion may be obtained by conventional Doppler techniques and the transverse and axial motion components used in quadrature to determine the true direction of motion. The inventive technique may be used to accurately produce the velocity and display the direction of moving fluids such as blood flow, and of moving tissue such as valves or the heart or vessel walls. The inventive technique may be used with both two dimensional and three dimensional ultrasonic images. The inventive technique may also be used with multiple sample volumes and spectral displays as described in U.S. Pat. No. 5,365,929.

The inventive system allows the simultaneous acquisition of the two receiving split apertures and the processing of a dual PW (pulse wave) signal (FIGS. 2 and 3). The two PW signals are then put in image memory from where they are collected and processed to get the absolute velocity and the direction of the flow. As the user moves the sample volume within a vessel, the angle correction will automatically track the direction and correct the velocity by the cosine of this direction angle. Thus, the user will have an automatic evaluation of the absolute velocity and the direction of the blood flow in real time.

What is claimed is:

1. An ultrasonic diagnostic imaging system which displays a measurement of flow or tissue motion comprising:
    an ultrasonic transducer array which transmits and receives ultrasonic signals;
    an image display;
    a signal processor, coupled to the transducer and the image display, which produces an image of a region of the body including moving fluids or tissue;
    a graphics display processor which produces an indicator on the moving element in the image that indicates the direction of fluid flow or tissue motion; and
    a vector processor which calculates the direction of fluid flow or tissue motion,
    wherein the direction of fluid flow or tissue motion indicated by the indicator is responsive to the direction of fluid flow or tissue motion calculated by the vector processor.

2. The ultrasonic diagnostic imaging system of claim 1, further comprising a velocity display processor, responsive to the ultrasonic signals, which produces a display of the speed of tissue or fluid motion,
    wherein the displayed speed is calculated in consideration of the direction calculated by the vector processor.

3. The ultrasonic diagnostic imaging system of claim 1, wherein the transducer array transmits beams to a sample volume location and receives echoes from the sample volume location in two or more sub-apertures.

4. The ultrasonic diagnostic imaging system of claim 3, wherein the vector processor is responsive to signals from the two sub-apertures to produce vector Doppler information relating to the sample volume location.

5. The ultrasonic diagnostic imaging system of claim 4, wherein the graphics display processor is responsive to the vector Doppler information to produce the indicator of the direction of fluid flow or tissue motion.

6. The ultrasonic diagnostic imaging system of claim 5, wherein the signal processor comprises a B mode processor and Doppler processor which produce the ultrasound image including the moving fluid or tissue and a spectral Doppler display of flow or motion at the sample volume location.

7. The ultrasonic diagnostic imaging system of claim 5, wherein the signal processor comprises a B mode processor and Doppler processor which produce the ultrasound image including the moving fluid or tissue and a color Doppler display of flow or motion within the ultrasound image.

8. The ultrasonic diagnostic imaging system of claim 1, wherein the vector processor comprises a speckle tracking processor.

9. The ultrasonic diagnostic imaging system of claim 1, wherein vector processor comprises a beam modulation processor.

10. A method for setting a flow direction indicator in an ultrasound image comprising:
    producing an ultrasound image including a vessel containing fluid flow;
    acquiring multiple echo signals from a sample volume location in the vessel;
    processing the multiple echo signals to produce motion vector data; and
    utilizing the motion vector data to set a flow direction indicator for the vessel.

11. The method of claim 10, further comprising utilizing the motion vector data to display flow velocity information.

12. The method of claim 10, further comprising producing a graphical flow direction indicator,
    wherein the graphical flow direction indicator is produced in response to the motion vector data.

13. The method of claim 12, wherein the graphical flow direction indicator is displayed on the vessel to indicate the direction of flow in the vessel.

14. The method of claim 10, wherein acquiring comprises receiving echo signals at two sub-apertures of a transducer array.

15. The method of claim 10, wherein processing comprises vector Doppler processing the multiple echo signals to determine the direction of flow.

16. The method of claim 10, wherein processing comprises determining the direction of flow by a non-Doppler technique.

17. The method of claim 16, wherein processing comprises tracking the speckle pattern of moving blood cells.

18. The method of claim 10, wherein processing comprises a beam modulation technique.

19. The method of claim 10, wherein producing comprises producing a three dimensional ultrasound image; and wherein acquiring comprises acquiring echo signals at two or more sub-apertures which are not co-aligned; and wherein processing produces motion vector data in three dimensions.

20. A method for indicating the direction of movement of moving tissue in an ultrasound image comprising:
    producing an ultrasound image including tissue which moves during the ultrasound procedure;
    acquiring multiple echo signals at two sub-apertures of a transducer array from a sample volume location coincident with the moving tissue;
    processing the multiple echo signals to produce motion vector data; and
    utilizing the motion vector data to indicate the direction of motion of the moving tissue.

21. The method of claim 20, further comprising utilizing the motion vector data to display tissue velocity information.

22. The method of claim 20, further comprising producing a graphical motion direction indicator,
    wherein the graphical motion direction indicator is produced in response to the motion vector data.

23. The method of claim 20, wherein the graphical motion direction indicator is displayed in association with the moving tissue in the ultrasound image to indicate the direction of movement of the tissue.

24. The method of claim 20, wherein processing comprises vector Doppler processing the multiple echo signals to determine the direction of tissue motion.

25. The method of claim 20, wherein processing comprises determining the direction of tissue motion by a non-Doppler technique.

26. The method of claim 25, wherein processing comprises tracking the speckle pattern of moving tissue.

27. The method of claim 20, wherein processing comprises a beam modulation technique.

28. The method of claim 20, wherein producing comprises producing a three dimensional ultrasound image; and wherein acquiring comprises acquiring echo signals at two or more sub-apertures which are not co-aligned; and wherein processing produces motion vector data in three dimensions.

* * * * *